United States Patent [19]

Pearson et al.

[11] 4,221,823

[45] Sep. 9, 1980

[54] PROCESS FOR MOUNTING PALYNOLOGICAL SPECIMENS

[75] Inventors: Michael B. Pearson; Sharon A. Meyer; Francis J. Shell, all of Bartlesville, Okla.

[73] Assignee: Phillips Petroleum Company, Bartleville, Okla.

[21] Appl. No.: 898,552

[22] Filed: Apr. 21, 1978

[51] Int. Cl.[2] .................... G01N 1/28

[52] U.S. Cl. .................... 427/4; 156/57; 424/3

[58] Field of Search .................... 427/2, 4; 424/3; 156/57; 350/92

[56] References Cited

U.S. PATENT DOCUMENTS

| | | | |
|---|---|---|---|
| 2,639,239 | 5/1953 | Elliott | 106/197 R |
| 2,753,273 | 7/1956 | Cohen et al. | 106/197 |
| 2,899,363 | 8/1959 | Nieburgs | 424/3 |
| 2,992,971 | 7/1961 | Millman et al. | 424/3 |
| 3,015,572 | 1/1962 | Casey et al. | 106/197 |

OTHER PUBLICATIONS

Jeffords et al., *Jour. of Paleontology,* "Preparation of Slides for Spores and Other Microfossils," vol. 33, pp. 344–347 (1959).

Hercules, Cellulose Gum–Chem. and Physical Properties, 1971.

Wilson, "A Water–Miscible Mountant for Palynology," *Oklahoma Geo. Survey,* vol. 19, pp. 110, 111, 1962.

Wilson, "Use of Hoyer's Soln. as a Palynological Mounting Medium," *Oklahoma Geo. Survey,* vol. 22, pp. 26–27, 1962.

Wilson, "New Water–Miscible Mountant for Palynology," *Micropaleonolgy,* vol. 14, pp. 247–248, 1968.

*Primary Examiner*—Lorenzo B. Hayes

[57] ABSTRACT

A process for mounting palynological specimen on a support employing a solution comprising water and at least one substance selected from the group consisting of water-soluble salts of carboxyalkyl hydroxyalkyl cellulose and water-soluble salts of carboxyalkyl cellulose.

18 Claims, No Drawings

PROCESS FOR MOUNTING PALYNOLOGICAL SPECIMENS

BACKGROUND OF THE INVENTION

This invention relates to a process, an article produced by the process and a composition of matter.

Palynology is defined as the study of pollen and spores, both modern and fossil pollen and spores. Although a relatively new science, palynology has rapidly become an important tool in the exploration for energy sources. Palynologists have discovered that fossil spores and pollen trapped in most coals, shale and sedimentary rock, yield valuable information in predicting the amount, type and distribution of petroleum that can be expected in a basin. Furthermore, palynological data is also useful in identifying geological features in wells and for unravelling the sedimentary history of basins.

To identify and draw conclusions from the pollen and spores, it is necessary to liberate trapped pollen and spores from the sedimentary sample. The method of liberating pollen and spores may be achieved by any of the chemical maceration processes known in the art. The basic principles of chemical maceration are outlined by J. B. Urban and J. K. Kline in "Chitinozoa of the Cedar City Formation, Middle Devonian of Missouri", Journal of Paleontology, Vol. 44, pp. 69–76 (1970). Briefly, sample materials are processed through hydrochloric acid, hydrofluoric acid, and Schultz's solution, leaving a chemically processed residue ready to be examined. The chemical nature of spores and pollen is such that most species are resistant to the destructive action of the corrosive acids. Since the examination and study of these acid-insoluble spores and pollen are almost totally microscopic, it is necessary that the microfossil residue be suitably mounted for microscopic analysis.

Several different media for mounting residues onto microscope slides exist. Exemplary mounting media are glycerin jelly, diaphane, Euparal, Canada balsam and hydroxyethyl cellulose (HEC).

Glycerin jelly has been one of the chief mounting media used in palynological studies, largely because of simplicity in use. However, glycerin jelly does not remain sufficiently set in warm climates, and thus the resulting slides are often difficult to preserve and file. Freezing, on the other hand, ruins glycerin jelly slides. Pollen and spore grains also have a tendency to swell and lose their characteristics in this medium. Furthermore, if the residue is not sufficiently dried before applying the glycerin jelly, air cavities develop which complicates specific microfossil identification.

Euparal and diaphane, also widely used, require time-consuming dehydration processes with alcohol. The chemically processed residue going into Euparal first requires dehydration with at least one charge of 95 percent methyl alcohol. As with glycerin jelly, care must be taken to allow the residue placed on the microscope slide to dry before adding the Euparal. Diaphane mounts may be prepared in essentially the same manner except that it is necessary to follow the alcohol treatment by a diaphane preparatory solution.

Some palynologists have made mounts with Canada balsam but the high index of refraction of this mounting medium is a disadvantage in most studies. Also Canada balsam, like diaphane, cannot be mixed directly with aqueous residues but requires dehydration with 95 percent methyl alcohol prior to mounting. Furthermore, slides prepared with Canada balsam have been observed to lose their permanency and begin to crack, discolor and crystallize after an extended period of time.

A 2 percent solution of hydroxyethyl cellulose (HEC) has been used for mounting polliniferous specimens, as detailed by R. M. Jeffords and D. H. Jones in "Preparation of Slides for Spores and Other Microfossils," Journal of Paleontology, Vol. 33, pp. 344–347 (1959). However, preparation of the HEC solution requires many time-consuming steps such as first saturating the HEC powder with methyl alcohol, stirring the admixture into distilled water, heating to remove the methanol, and then filtering to eliminate insoluble, fibrous particles.

Although most of the above described mounting methods and medium have some advantageous features, there is a need for an improved method for simply obtaining permanent slides.

Accordingly, it is an object of this invention to provide a simple process for mounting specimens on a support.

Another object of this invention is to provide a solution suitable for mounting specimens on a support.

Another object of this invention is a simply prepared permanently mounted slide.

Other aspects, objects and advantages of the invention will be apparent to one skilled in the art upon study of the disclosure and the appended claims.

SUMMARY OF THE INVENTION

In accordance with the present invention a solution is prepared by admixing water and at least one substance selected from the group consisting of water-soluble salts of carboxyalkyl hydroxyalkyl cellulose and water-soluble salts of carboxyalkyl cellulose wherein the amount of the water-soluble salt is within the range of about 0.3 to about 1.5 weight percent based on the weight of the solution, and thereafter placing at least a portion of said solution on a support along with a suitable amount of a specimen.

Further according to the invention a solution comprises water and at least one substance selected from the group consisting of water-soluble salts of carboxyalkyl hydroxyalkyl cellulose and water-soluble salts of carboxyalkyl cellulose wherein the amount of the water-soluble salt is within the range of about 0.3 to about 1.5 weight percent based on the weight of the solution.

Still further according to this invention an article comprises a support, a specimen and a film which is employed to attach said specimen to said support, said film being formed by evaporating water from a solution comprising water and at least one substance selected from the group consisting of watersoluble salts of carboxyalkyl hydroxyalkyl cellulose and water-soluble salts of carboxyalkyl cellulose wherein the amount of the water-soluble salt is within the range of about 0.3 to about 1.5 weight percent based on the weight of the solution.

This invention achieves more economical operations and increased ease in slide preparation than has previously been known in the art. Expensive chemicals and time-consuming steps, such as the chemical dehydration of residues prior to mounting, are eliminated. Moreover, preparation of the solution of this invention does not require the use of wetting agents such as methyl alcohol or other extraneous steps such as heating and filtration. Further, slides prepared according to the present invention can be kept indefinitely in excellent condition at normal room temperature.

DETAILED DESCRIPTION OF THE INVENTION

The water-soluble salts of carboxyalkyl hydroxyalkyl cellulose that can be used in the practice of this invention are selected from ammonium salts of carboxymethyl hydroxyethyl cellulose (CMHEC), carboxyethyl hydroxyethyl cellulose and carboxymethyl hydroxymethyl cellulose and metal salts of Group IA metals of carboxymethyl hydroxyethyl cellulose (CMHEC), carboxyethyl hydroxyethyl cellulose and carboxymethyl hydroxymethyl cellulose.

The water-soluble salts of carboxyalkyl cellulose that can be used in the practice of this invention are selected from ammonium salts of carboxymethyl cellulose (CMC), carboxyethyl cellulose and carboxypropyl cellulose and metal salts of Group IA metals of carboxymethyl cellulose (CMC), carboxyethyl cellulose and carboxypropyl cellulose.

As used herein, the term Group IA metals denotes the metals of the Periodic Table of the Elements as presented at page B-2 of the "Handbook of Chemistry and Physics", 45th Edition, 1964.

Presently preferred Group IA metals are sodium, potassium and lithium.

The preferred water-soluble salt of carboxyalkyl cellulose is sodium carboxymethyl cellulose because it is readily available, comparatively inexpensive and it has been used with good results.

Water-soluble carboxymethyl cellulose is available in various degrees of substitution. The term "degree of substitution", as used herein, means the average number of sites on each molecule actually occupied by a sodium carboxymethyl unit. For complete substitution, the degree of substitution is 3.0. A sodium salt of carboxymethyl cellulose having a degree of substitution greater than about 0.3 is generally water soluble or water dispersible.

Any water-soluble sodium carboxymethyl cellulose can be used in the invention. Generally the sodium carboxymethyl cellulose has a degree of substitution in the range of 0.3 to 3.0, preferably 0.7 to 1.2. However, the sodium CMC having a degree of substitution of 0.9 is preferred because of superior operability. The degree of substitution of sodium carboxymethyl cellulose is commonly designated in practice as CMC-7, CMC-9, CMC-12, etc. where the 7, 9, and 12 refer to a degree of substitution of 0.7, 0.9 and 1.2, respectively.

Additional information on the various properties of sodium CMC or cellulose gums is also available in "Hercules Cellulose Gum—Properties and Uses", copyright Hercules Powder Company, 1960 and in "Hercules Cellulose Gum," copyright by Hercules Incoporated, 1968.

The aqueous solution of the invention is formed by admixing a measured quantity of water-soluble salt into a measured volume of water. The amount of the water-soluble salt used in the practice of the invention is generally within the range of about 0.3 to about 1.5, preferably from about 0.4 to about 0.8, more preferably from about 0.4 to about 0.6, weight percent, based on the weight of the solution. Solutions having a higher concentration of water-soluble salts, i.e. from about 1.5 to about 0.8 weight percent, had a high viscosity which hampered spreading the specimen on the support. Above 1.5 weight percent, insoluble particles, commonly referred to as "fisheyes", appeared in the solution and interfered with the identification of the specimens. A 0.6 weight percent solution was found to be particularly effective for evenly dispersing a specimen. The 0.4 weight percent solution showed some tendency in allowing specimen flocculation whereas the 0.2 weight percent solution demonstrated no dispersing properties due to heavy specimen flocculation.

Although not required, it is presently preferred that distilled water be used. Tap water may contain impurities and contaminants, such as pollen grains, that complicate accurate palynological microfossil identification.

Mixing time can vary widely depending on the amount of water-soluble salt employed. Generally, the time required ranges from about 10 minutes to about 1 hour.

Following preparation of the solution, at least a portion of said solution is placed on a support along with a suitable amount of a specimen. Of course, the volumes of solution and specimen that are needed depend on the area of the support.

A preferred support is at least one light transmitting plate. More specifically, such a support includes, but is not limited to, a cover glass superposed on a glass microscope slide. Presently preferred are the cover glasses and glass slides that are described in ASTM E 211-70, Part 42 (1977).

Specimens that can be used in this invention are those selected from the group consisting of microorganisms and microfossils.

Suitable microfossils include nannoplanktons, dinoflagellates, silicoflagellates, coccoliths, discoasterids, thallophytes such as bacteria, algae, and fungi, protozoa such as foraminifers and radiolarians, echinoderms such as microblastoids and microcrinoids, bryozoans, spores and pollen, mineral seeds, organic fragments and debris, internal structures of woods, and porifers such as sponge spicules.

Suitable microorganisms include nannoplanktons, dinoflagellates, silicoflagellates, coccoliths, discoasterids, thallophytes such as bacteria, algae, and fungi, protozoa such as foraminifers and radiolarians, echinoderms such as microblastoids and microcrinoids, bryozoans, and spores and pollen.

The presently preferred microfossils are the acid insoluble spores, pollen, organic fragments and debris.

The acid-insoluble microfossils are those chemically extracted from sample materials, such as shales, clays, sillstones, coals, lignites, and mudstone. The preferred chemical maceration process for liberating these acidinsoluble microfossils involves crushing and thoroughly mixing individual rock samples. The mixed sample is covered with about 150 ml of dilute 38 percent hydrochloric acid for about 12 to 24 hours to remove carbonates. Distilled water is added and decanated until the liquid is neutral. The residue is then covered with approximately 150 ml of 52 percent hydrofluoric acid for about 36 to 48 hours to remove silicates. Distilled water is added and decanted until the liquid is neutral. Zinc bromide, with a specific gravity of about 2.0, is added to the solution and centrifuged for about 20 minutes to separate the lighter organics. The heavier organic material is precipitated. About half of the lighter organic material, commonly called kerogen, is diluted in distilled water and can be mounted on a support with the water soluble salts of this invention. Kerogen slide is essentially a mixture of organic fragments, spores, pollen, resins, cutin, and waxes.

To the remaining half of the lighter organic is added Schultz's solution. After about 30 minutes, the liquid is decanted and the procedure is repeated until the liquid is neutral. Approximately 100 ml of a 10 percent solution of potassium hydroxide is then added to the solution. After two minutes, the liquid is decanted until the solution is neutral. Following this chemical treatment, the solution can then be stained with a safranine solution. The specimen is then ready to be mounted.

A portion of the water-soluble salt solution of the present invention is then placed on the support along with a suitable amount of the specimen and admixed. The admixture is then allowed to air-dry to a hard film. The drying may be speeded by heating the solution on the support in an oven or on a hot plate at a temperature of approximately 40°-60° C. The water is evaporated from the admixture, thereby forming a film on said support. The support can then be examined under the microscope.

The following examples illustrate the invention.

EXAMPLE I

A series of runs was carried out to illustrate the effect of varying the concentration of sodium carboxymethyl cellulose for mounting specimens. A 1.5 weight percent sodium CMC solution was prepared by slowly sifting 4.2 grams of sodium CMC-9 into 280 grams of distilled water while stirring at room temperature with a Hamilton Beach malt mixer. The malt mixer was connected to a rheostat so that the speed of rotation could be controlled. Initially the powerstat was set on 50 percent and the power gradually increased as the viscosity of the solution increased. The total time for complete mixing took nearly one hour.

A specimen solution comprising acid-insoluble microfossils and other associated organic debris and fragments was extracted from various rock samples by the chemical maceration techniques previously discussed in the specification. Following the chemical treatment, 1-2 drops of the specimen solution were placed on a cover glass. The cover glass was superposed on a glass slide. Thereafter, 1-2 drops of the 1.5 weight percent sodium CMC-9 solution were placed on the cover glass. The specimen and sodium CMC solutions were then admixed with a small needle and spread evenly over the entire surface of the cover glass. The glass slide was placed on a hot plate for about 30 minutes to 1 hour at 60° C. to evaporate the water from the admixture. After the admixture dried, a thin film formed on the cover glass. The cover glass was removed from the glass slide, inverted, and replaced on the glass slide over a drop of "Permount", a toluene based glue. The slide was then examined under a microscope.

Solutions having a concentration of 1.0, 0.8, 0.6, 0.4 and 0.2 weight percent sodium CMC in water were prepared by dilution of the 1.5 weight percent sodium CMC-9 solution described above using a Mettler balance to weigh both the water and the solution. The procedure outlined above for slide preparation was repeated for each of the various sodium CMC solutions.

Slides made from the 1.5 and 1.0 through 0.4 weight percent sodium CMC-9 solutions were satisfactory in adhering the microfossils to the cover glass. These solutions kept the microfossils dispersed and evenly distributed across the cover glass. However, with solutions having a higher concentration of sodium CMC-9, viz., 1.5, 1.0, and 0.8, the high viscosity caused difficulty in spreading the solutions containing the microfossils across the cover glass. When many slides are to be made in one day this would materially increase the time necessary to make the slides. The 0.6 weight percent solution was found to be particularly effective in dispersing the microfossils. The 0.4 weight percent solution showed some tendency in allowing the microfossils to flocculate. The 0.2 weight percent solution demonstrated no dispersing properties due to heavy microfossil flocculation. The 0.2 weight percent solution was considered unacceptable for palynological studies.

Thus, based on these runs, and other data herein, it is concluded that the amount of the water soluble salt used in the practice of the invention should be within the range of about 0.3 to about 1.5, preferably from about 0.4 to about 0.8, more preferably from about 0.4 to about 0.6, weight percent, based on the weight of the solution.

EXAMPLE II

A series of runs was carried out to illustrate the effect of prewetting the CMC-9 with methyl alcohol. Three 0.57 weight percent sodium CMC solutions were separately prepared by adding 1.60 grams of sodium CMC-9 into 280 grams of distilled water while stirring at room temperature with a Hamilton Beach malt mixer. Two of these solutions were prepared by initially prewetting the sodium CMC-9 powder with methanol; the third solution was prepared in the preferred manner i.e., without methanol. The total time for mixing took about 10 minutes for each solution. The methyl alcohol was removed from one of the solutions by heating and left in the other. The procedure outlined in Example I for slide preparation was repeated for each of the three sodium CMC solutions.

The sodium CMC solution containing the methyl alcohol was unacceptable for slide preparation because it caused flocculation of the microfossils. When the methanol was removed by heating, the solution was found to be acceptable for palynological studies. The sodium CMC solution prepared without methanol was particularly effective in spreading and adhering the microfossils to the cover glass. Thus, it is concluded that methanol adds nothing to the sodium CMC solution except the expense of the methanol and expense of removing it. Furthermore, it makes the final concentration of the solution inexact since some of the water is removed as the methanol is boiled off.

EXAMPLE III

In this example a 2 weight percent solution of CMC-9 in water was prepared. 5.6 Grams of sodium CMC-9 was prewetted with methyl alcohol to accelerate dispersion. The sodium CMC-9 was slowly added into 280 grams of distilled water while stirring at room temperature with a Hamilton Beach malt mixer. The total time for complete mixing was three days.

Although it was possible to prepare a 2 weight percent solution of sodium CMC, three days was necessary to dissolve insoluble particles which would otherwise interfere with the interpretation of palynological slides. Furthermore, due to the high viscosity of the 2 weight percent solution it was extremely difficult to spread the specimen across the support.

Reasonable variations and modifications, which will be apparent to those skilled in the art, can be made in this invention without departing from the spirit and scope thereof.

We claim:

1. A process comprising:

forming a solution comprising water and at least one water-soluble salt selected from the group consisting of carboxymethyl cellulose, carboxyethyl cellulose, carboxypropyl cellulose, carboxymethyl hydroxyethyl cellulose, carboxyethyl hydroxyethyl cellulose, and carboxymethyl hydroxymethyl cellulose wherein the amount of the water-soluble salt is within the range of about 0.3 to about 1.5 weight percent based on the weight of the solution, placing at least a portion of said solution on a support along with a suitable amount of a specimen.

2. A process according to claim 1 further comprising evaporating the water from said solution to produce a film which secures said specimen to said support.

3. A process according to claim 2 wherein said water is evaporated by heating said support after said solution and said specimen are placed thereon.

4. A process according to claim 3 wherein said support is at least one light-transmitting plate.

5. A process according to claim 4 wherein said support is a cover glass.

6. A process according to claim 1 wherein said water is distilled water.

7. A process according to claim 1 wherein the amount of watersoluble salt is within the range of about 0.4 to about 0.8 weight percent based on the weight of the solution.

8. A process according to claim 1 wherein the amount of watersoluble salt is within the range of about 0.4 to about 0.6 weight percent based on the weight of the solution.

9. A process according to claim 1 wherein the water-soluble salts are selected from the group consisting of metal salts of Group IA metals of the Periodic Table of the Elements and ammonium salts.

10. A process according to claim 9 wherein the Group IA metals are selected from the group consisting of lithium, sodium, and potassium.

11. A process according to claim 10 wherein the water-soluble salt is sodium carboxymethyl cellulose.

12. A process according to claim 11 wherein said sodium carboxymethyl cellulose has a degree of substitution in the range of 0.7 to 1.2.

13. A process according to claim 12 wherein said sodium carboxymethyl cellulose has a degree of substitution of about 0.9.

14. A process according to claim 5 wherein said support is a cover glass attached to a glass slide wherein the specimen is positioned between said cover glass and said glass slide.

15. A process according to claim 1 wherein said solution is formed consisting essentially of said water and said at least one water-soluble salt.

16. A process according to claim 1 wherein said specimen is selected from the group consisting of microorganisms and microfossils.

17. A process according to claim 16 wherein said microfossils are acid-insoluble.

18. A process according to claim 1 wherein said water is distilled water, said water-soluble salt is sodium carboxymethyl cellulose having a degree of substitution of about 0.9 wherein the amount of said sodium carboxymethyl cellulose is within the range of about 0.4 to about 0.6 weight percent based on the weight of the solution, said support is a cover glass and said specimen is an acid-insoluble microfossil.

* * * * *